US010830722B2

(12) United States Patent
Yassine et al.

(10) Patent No.: US 10,830,722 B2
(45) Date of Patent: Nov. 10, 2020

(54) GAS SENSORS AND METHODS OF DETECTING GAS

(71) Applicant: King Abdullah University of Science and Technology, Thuwal (SA)

(72) Inventors: Omar Yassine, Thuwal (SA); Osama Shekhah, Thuwal (SA); Youssef Belmabkhout, Thuwal (SA); Mohamed Eddaoudi, Thuwal (SA); Khaled N. Salama, Thuwal (SA)

(73) Assignee: KING ABDULLAH UNVIERSITY OF SCIENCE AND TECHNOLOGY, Thuwal (SA)

( * ) Notice: Subject to any disclaimer, the term of this patent is extended or adjusted under 35 U.S.C. 154(b) by 266 days.

(21) Appl. No.: 15/797,933

(22) Filed: Oct. 30, 2017

(65) Prior Publication Data

US 2018/0195990 A1 Jul. 12, 2018

Related U.S. Application Data

(60) Provisional application No. 62/444,028, filed on Jan. 9, 2017.

(51) Int. Cl.
*G01N 33/00* (2006.01)
*G01N 27/12* (2006.01)
*G01N 27/22* (2006.01)

(52) U.S. Cl.
CPC ......... *G01N 27/125* (2013.01); *G01N 27/128* (2013.01); *G01N 27/226* (2013.01); *G01N 27/227* (2013.01); *G01N 33/0044* (2013.01); *G01N 33/0054* (2013.01); *Y02A 50/246* (2018.01)

(58) Field of Classification Search
CPC .... G01N 27/12; G01N 27/227; G01N 27/226; G01N 33/0054; G01N 33/0044; Y02A 50/246
See application file for complete search history.

(56) References Cited

U.S. PATENT DOCUMENTS

| 4,703,646 | A | 11/1987 | Muller |
| 6,111,280 | A | 8/2000 | Gardner et al. |
| 6,341,629 | B1 | 1/2002 | Clark et al. |
| 2007/0202012 | A1 | 8/2007 | Steichen |
| 2008/0220535 | A1 | 9/2008 | LeBoeuf |
| 2010/0132547 | A1 | 6/2010 | Masel |
| 2011/0077447 | A1 | 3/2011 | Groothuis et al. |
| 2011/0174799 | A1 | 7/2011 | Ali |
| 2012/0116683 | A1 | 5/2012 | Potyrailo |
| 2015/0020577 | A1* | 1/2015 | Luebke ............... G01N 27/12 73/31.06 |

FOREIGN PATENT DOCUMENTS

| DE | 102009047201 A1 | 6/2011 |
| EP | 2087916 A1 | 8/2009 |
| WO | 2010078337 A1 | 7/2010 |
| WO | 2011136440 A1 | 11/2011 |

OTHER PUBLICATIONS

"Examination Report", Gulf Cooperation Council Patent Application No. 2013-23441, dated Jun. 29, 2016, 4 pages.
"Extended European Search Report", European Application No. 13761034.1, dated Aug. 25, 2015, 9 pages.
"International Search Report and Written Opinion", International Application No. PCT/US2013/023764, dated Jun. 28, 2013, 12 pages.
Achmann, et al., "Metal-Organic Frameworks for Sensing Applications i n the Gas Phase", Sensors, vol. 9, No. 3, Mar. 6, 2009, 1574-1589.
Allendorf, et al., "A Roadmap to Implementing Metal—Organic Frameworks in Electronic Devices: Challenges and Critical Directions", Chem. Eur. J., 2011, 17, 11372-11388.
Asad, et al., "High sensitive and selective flexible H2S gas sensors based on Cunanoparticle decorated SWCNTs", Sensors and Actuators B 210 (2015) 1-B.
Asad, et al., "Highly sensitive wireless H2S gas sensors at room temperature basedon CuO-SWCNT hybrid nanomaterials", Sensors and Actuators B 231 (2016) 474-483.
Baca, et al., "Rapid detection of ebola virus with a reagent-free, point-of-care biosensor", Sensors (2015), 15: 8605-8614.
Choi, et al., "Facile Au catalyst loading on the inner shell of hollow SnO2 spheres using Au-decorated block copolymer sphere templates and their selective H2S sensing characteristics", Nanoscale, 2014, 6, 11898-11903.
Choi, et al., "Highly Efficient Electronic Sensitization of Non-oxidized Graphene Flakes on Controlled Pore-loaded WO3 Nanofibers for Selective Detection ofH2S Molecules", Scientific Reports, 5, 8067, Jan. 28, 2015, 1-9.
Crowley, et al., "Fabrication of Polyaniline-Based Gas Sensors Using Piezoelectric Inkjet and Screen Printing for the Detection of Hydrogen Sulfide", IEEE Sensors Journal, vol. 10, No. 9, Sep. 2010, 1419-1426.
Cui, et al., "Resonant tunneling modulation in quasi-2D Cu2O/SnO2 p-n horizontalmulti-layer heterostructure for room temperature H2S sensor application", Scientific Reports, 3, 1250, Feb. 13, 2013, 1-8.
Eddaoudi, et al., "Systematic Design of Pore Size and Functionality in Isoreticular MOFs and Their Application in Methane Storage", Science, vol. 295, Jan. 18 2002, 469-472.

(Continued)

*Primary Examiner* — Christopher Adam Hixson
(74) *Attorney, Agent, or Firm* — Billion & Armitage; Gregory S. Schwartz

(57) ABSTRACT

Embodiments of the present disclosure describe a gas sensor comprising a gas-sensing material including a metal-organic framework with fcu topology and a substrate with a pair of electrodes proximate to the gas-sensing material, wherein the gas sensor is configured to detect toxic gas. Embodiments of the present disclosure further describe a method of detecting gas comprising contacting a gas sensor including a metal-organic framework with fcu topology with a gas/vapour composition including at least one toxic gas, capturing the at least one toxic gas from the fluid composition, and measuring an electrical property to detect a presence of the at least one toxic gas.

18 Claims, 15 Drawing Sheets

(56) References Cited

OTHER PUBLICATIONS

EP App. No. 13761034.1, "Extended European Search Report", dated Aug. 25, 2015, 9 pages.

Fedder, et al., "Technologies for Cofabricating MEMS and Electronics", Proceedings of the IEEE, vol. 96, No. 2, pp. 306-322, 2008.

Fu, et al., "High response and selectivity of a Cu—ZnO nanowire nanogenerator as a self-powered/ active H2S sensor", Phys. Chem. Chem. Phys., 2015, 17, 2121-2126.

Gardner, et al., "CMOS interfacing for integrated gas sensors: A review.", IEEE Sensors Journal, vol. 10, No. 12, pp. 1833-1848, 2010.

Ghafar-Zadeh, et al., "Cmos capacitive sensors for lab-on-chip applications: A multidisciplinary approach", Springer, 2010.

Girija, et al., "Highly selective H2S gas sensor based on Cu-doped ZnO nanocrystalline films deposited by RF magnetron sputtering of powder target", Journal of Alloys and Compounds 684 (2016) 15-20.

Glass, "A Reviwe of the Health Effects of Hydrogen Sulphide Exposure", Ann. Occup. Hyg., vol. 34, No. 3, pp. 323-327, 1990.

Goldoni, et al., "Sensing gases with carbon nanotubes: A review of the actual situation", Journal of Physics Condensed Matter, vol. 22, No. 1, 2010.

Grover, "Interdigitated Array Electrode Sensors: Their Design, Efficiency, and Applications", University of Tennessee Honors Thesis Projects, May 10, 1999, 62 pages.

Hagleitner, et al., "Smart single-chip gas sensor microsystem", Nature, 414, Nov. 15, 2001, 293-296.

Hazardous Substances Databank, "Hydrogen sulfide", National Library of Medicine, Bethesda, MD, USA, 2011, <https://toxnet.nlm.nih.gov/cgi-bin/sis/search/a?dbs+hsdb:@term+@DOCNO+576, accessed Feb. 13, 2017>.

Hierlemann, et al., "CMOS-based chemical microsensors", Analyst, 2003, 128, 15-28.

Joo, et al., "Chemical Sensors with Integrated Electronics", Chemical Reviews, 2008, 108, 2, 638-651.

Kaur, et al., "Room-temperature H2S gas sensing at ppb level by single crystal In2O3 whiskers", Sensors and Actuators B 133 (2008) 456-461.

Kim, et al., "Characterization of malodorous sulfur compounds in landfill gas", Atmospheric Environment 39 (2005) 1103-1112.

Kim, et al., "The emission characteristics and the related malodor intensities of gaseous reduced sulfur compounds (RSC) in a large industrial complex", Atmospheric Environment 40 (2006) 4478-4490.

Kreno, et al., "Metal-Organic Framework Materials as Chemical Sensors", Chemical Reviews, vol. 112, No. 2, Feb. 8, 2012, 1105-1125.

Li, et al., "Resistive gas sensors based on colloidal quantum dot (CQD) solids forhydrogen sulfide detection", Sensors and Actuators B 217 (2015) 198-201.

Ma, et al., "a-Fe2O3 nanochains: ammonium acetate-based ionothermal synthesis and ultrasensitive sensors for low-ppm-level H2S gas", Nanoscale, 2013, 5, 895-898.

Ma, et al., "Room temperature ppb level H2S detection of a single Sb-doped SnO2nanoribbon device", Sensors and Actuators B 216 (2015) 72-79.

McKinlay, et al., "BioMOFs: Metal-Organic Frameworks for Biological and Medical Applications", Angew. Chem. Int. Ed., 2010, 49, 6260-6266.

Meek, et al., "Metal-Organic Frameworks: A Rapidly Growing Class of Versatile Nanoporous Materials", Adv. Mater. 2011, 23, 249-267.

Osha, Occupational Safety and Health Administration, Fact sheet of Hydrogen sulfide (H2S), DSG Oct. 2005 <http://www.osha.-gov/OshDoc/data_Hurricane_Facts/hydrogen_sultide_fact.pdf>.

Pohle, et al., "Metal Organic Frameworks as promising High Surface Area Material for Work Function Gas Sensors", Procedia Engineering, vol. 25, Jan. 8, 2012, 108-111.

Potyrailo, et al., "Materials and Transducers Toward Selective Wireless Gas Sensing", Chem Rev., Nov. 9, 2011, 111(11), 7315-7354.

Ratinac, et al., "Toward ubiquitous environmental gas sensors—Capitalizing on the promise of graphene", Environmental Science and Technology, vol. 44, No. 4, pp. 1167-1176, 2010.

Rheaume, et al., "A review of recent progress in sensing of gas concentration by impedance change", Ionics, vol. 17, No. 2, pp. 99-108, 2011.

Sapsanis, et al., "Insights on Capacitive Interdigitated Electrodes Coated with MOF Thin Films: Humidity and VOCs Sensing as a Case Study", Sensors 2015, 15, 18153-18166.

Sarfraz, et al., "Printed hydrogen sulfide gas sensor on paper substrate based on polyaniline composite", Thin Solid Films 534 (2013) 621-628.

Shekhah, et al., "MOF thin films: existing and future applications", Chem. Soc. Rev. 2011, 40, 1081-1106.

Wales, et al., "Gas sensing using porous materials for automotive applications", Chem. Soc. Rev., 2015, 44, 4290-4321.

Wu, et al., "Stably dispersed carbon nanotubes covalently bonded to phthalocyanine cobalt(II) for ppb-level H2S sensing at room temperature", J. Mater. Chem. A, 2016, 4, 1096-1104.

Xue, et al., "Tunable Rare Earth fcu-MOF Platform: Access to Adsorption Kinetics Driven Gas/Vapor Separations via Pore Size Contraction", J. Am. Chem. Soc., 2015, 137, 5034-5040.

Yoem, et al., "Enhanced toxic gas detection using a MEMS preconcentrator coated with the metal organic framework absorber", IEEE 21st International Conference on Micro Electro Mechanical Systems, 2008, 232-235.

Yu, et al., "Low concentration H2S detection of CdO-decorated hierarchicallymesoporous NiO nanofilm with wrinkle structure", Sensors and Actuators B 230 (2016) 706-713.

Zhang, et al., "Chemical and biological technologies for hydrogen sulfide emission control in sewer systems: A review", Water Research 42 ( 2008) 1-2.

"Toxicological Review of Hydrogen Sulfide", US Environmental Protection Agency, Washington, DC USA, 2003.

Alammar, et al., "Ultrasound-assisted synthesis of mesoporous B—Ni(Oh)2 and NiO nano-sheets using ionic liquids", J. Mater. Chem., 22, 2012, 18252-18260.

Assen, et al., "Ultra-Tuning of the Rare-Earth fcu-MOF Aperture Size for Selectrive Molecular Exclusion of Branched Paraffins", Angew. Chem, 127, 2015, 14561-14566.

Zhou, et al., "Introduction to Metal-Organic Frameworks", Chem. Rev. 2012, 112, 673-674, 2012, 673-674.

Azzam, et al., "Fabrication of a surface plasmon resonance biosensor based on gold nanoparticles chemisorbed onto a 1,10-decanedithiol self-assembled monolayer", Thin Solid Films, 518, 2009, 387-391.

Bracke, et al., "Ultra-Low-Power Interface Chip for Autonomous Capacitive Sensor Systems", IEEE Transactions on Circuits and Systems—I: Regular Papers, vol. 54, No. 1, Jan. 2007, 130-140.

Gauglitz, "Direct optical sensors: principles and selected applications", Anal. Bioanal. Chem. 381, 2005, 141-155.

Guth, et al., "Recent Developments in electrochemical sensor application and technology—a review", Meas. Sci. Technol, 20, 2009, 1-14.

Kuppler, et al., Coordination Chemistry Reviews 253 (2009) 3042-3066, 2009, 3042-3066.

Kuppler, et al., "Potential applications of metal-organic frameworks", Coordination Chemistry Reviews, 2009, 253, 3042-3066, 2009, 3042-3066.

Li, et al., "Carbon Nanotube Sensors for Gas and Organic Vapor Detection", Nano Letters, vol. 3, No. 7, 2003, 929-933.

Llobet, "Gas sensors using carbon nanomaterials: A review", Sensors and Actuators, B, 179, 2013, 32-45.

Omran, et al., "An integrated energy-efficient capacitive sensor digital interface circuit", Sensors and Actuators, A, 216, 2014, 43-51.

Pandey, et al., "A Review of methods for the determination of reduced Sulfur Compounds (RSCs) in Air", Environ. Sd. Technol., 43 2009, 3020-3029.

(56) References Cited

OTHER PUBLICATIONS

Pavinatto, et al., "Printed and flexible biosensor for antioxidants using interdigitated ink-jetted electrodes and gravure-deposited active layer", Biosensors and Bioelectronics, 67, 2015, 553-559.

Samai, et al., "A light responsive two-component supramolecular hydrogel: a sensitive platform for the fabrication of humidity sensors", Soft Matter, 12, Feb. 15, 2016, 2842-2845.

Shekhah, et al., "Grafting a Monocarboxylic Substituted Polychlorotriphenylmethyl Radicals onto a COOH-Functionalized Self-Assembled Monolayer through Copper (II) Metal Ions", Langmuir, 24, 2008, 6640-6648.

Shekhah, et al., "Post-synthetic modification of epitaxially grown, highly oriented functionalized MOF thin films", www.rsc.org/chemcomm, DOI: 10.1039/c1cc12543e, Chemical Communications—Sep. 2011, 2011, 1120-11212.

Shekhah, et al., "Successful implementation of the stepwise layer-by-layer growth of MOF thin films on confined surfaces: mesoporous silica foam as a first case study", Chem. Commun., 48, 2012, 11434-11436.

Shekhah, et al., "The liquid phase epitaxy method for the construction of oriented ZIF-8 thin films with controlled growth on functionalized surfaces", Chem. Commun., 2013, 49, 10079, 2013, 10079-10081.

Stetter, et al., "Sensors, Checmical Sensors, Electrochemical Sensors, and ECS", Journal of the Electrochemical Society, 150, (2), 2003, S11-S16.

Streit, et al., "Surface-Anchored MOF-Based Photonic Antennae", ChemPhysChem Articles, 13, 2012, 2699-2702.

Tsouti, et al., "Capacitive microsystems for biological sensing", Biosensors and Bioelectronics, 27, 2011, 1-11.

Xue, et al., "Tunable Rare-Earth fcu-MOFs: A Platform for Systematic Enhancement of $CO_2$ Adsorption Energetics and Uptake", J. Am. Chem. Soc., vol. 135,, Apr. 22, 2013, 7660-7667.

* cited by examiner

GAS SENSORS AND METHODS OF DETECTING GAS

This application claims benefit of U.S. Provisional Application No. 62/444,028, filed on Jan. 9, 2017 and which application is incorporated herein by reference. A claim of priority is made.

BACKGROUND

Chemical sensors have been utilized to detect toxic gas. For example, gas chromatography-based methods have been used to monitor $H_2S$ and $NH_3$ for environmental settings. While precise, these methods are challenging, impractical, and require multi-stage protocols, limiting these methods ability to monitor short-term variations in $H_2S$ and $NH_3$ levels due to changes in environmental conditions. Other sensors have been utilized for real-time detection of toxic gas. These sensors are largely based on semiconducting metal oxides sensors, electrochemical sensors, optical sensors, and sensor arrays. However, consistency is a significant problem, as the performance of these sensors may vary widely. As an alternative, chemical sensors have been fabricated based on principles of colorimetry and spectroscopy. However, colorimetric sensors, for example, cannot be easily integrated with electronics in a miniaturized microsystem.

It therefore would be desirable to detect toxic gas via a gas sensor that may be integrated with electronics in a miniaturized microsystem and that consistently exhibits a high sensitivity and high selectivity towards toxic gas.

SUMMARY

In general, embodiments of the present disclosure describe gas sensors and methods of detecting gas.

Accordingly, embodiments of the present disclosure describe a gas sensor comprising a gas-sensing material including a metal-organic framework with fcu topology and a substrate with a pair of electrodes proximate to the gas-sensing material, wherein the gas sensor is configured to detect toxic gas.

Embodiments of the present disclosure also describe a gas sensor for detecting $H_2S$ and/or $NH_3$ comprising: a gas-sensing material including a rare earth metal-organic framework with fcu topology (RE-fcu-MOF), wherein the ligand of the RE-fcu-MOF is one or more of fumaric acid and 1,4-napthalene dicarboxylic acid; and a substrate with a pair of electrodes, wherein the pair of electrodes is proximate to the gas-sensing material; wherein the gas sensor is configured to detect one or more of $H_2S$ and $NH_3$.

Embodiments of the present disclosure further describe a method of detecting gas comprising contacting a gas sensor including a metal-organic framework with fcu topology with a gas/vapour composition including at least one toxic gas, capturing the at least one toxic gas from the gas/vapour composition, and measuring an electrical property to detect a presence of at least one toxic gas.

Embodiments of the present disclosure also describe a method of detecting gas comprising contacting a gas sensor including a rare earth metal-organic framework with fcu topology (RE-fcu-MOF) with a fluid composition including one or more of $H_2S$ and $NH_3$ and at least one other chemical species; capturing one or more of $H_2S$ and $NH_3$ from the fluid composition; and measuring an electrical property to detect a presence of one or more of $H_2S$ and $NH_3$.

The details of one or more examples are set forth in the description below. Other features, objects, and advantages will be apparent from the description and from the claims.

BRIEF DESCRIPTION OF DRAWINGS

This written disclosure describes illustrative embodiments that are non-limiting and non-exhaustive. In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

Reference is made to illustrative embodiments that are depicted in the figures, in which.

DETAILED DESCRIPTION

Figure 1:
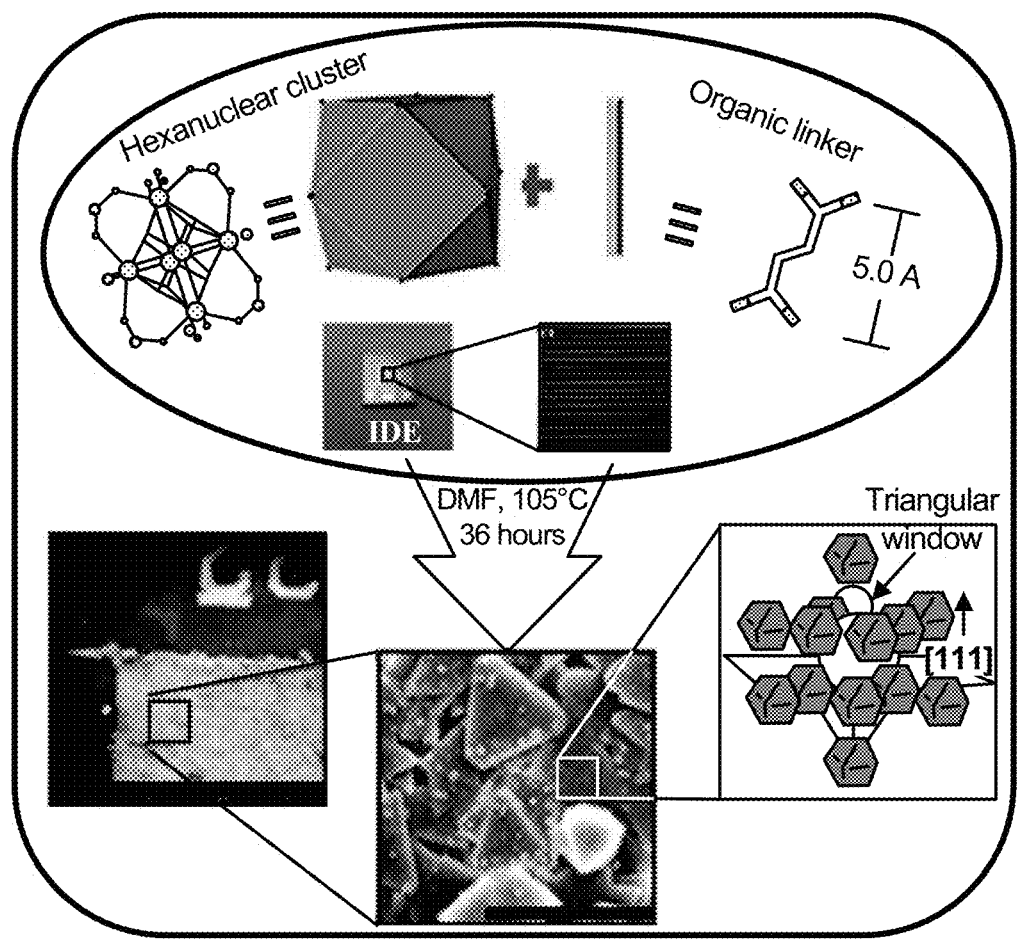
FIG. 1 is a schematic diagram of an optimized solvothermal preparation approach of a fumarate-based fcu-MOF (fum-fcu-MOF) thin film on an interdigitated electrode (IDE), according to one or more embodiments of the present disclosure.

The invention of the present disclosure relates to gas sensors for detecting a presence of toxic gas. In particular, the gas sensors of the present disclosure include a gas-sensing material including a metal-organic framework with fcu topology and a substrate with a pair of electrodes proximate to the gas-sensing material. To detect toxic gases, a vapour composition including toxic gas may be contacted with the gas sensor. Due to the selectivity of the gas-sensing material towards toxic gas, the toxic gas may be captured by the gas sensor via diffusion, adsorption, and/or chemical reaction, for example. The diffusion, adsorption, and/or chemical reaction of the toxic gas may produce a measurable change in an electrical property of the gas sensor that may be utilized to detect a presence of toxic gas. In this way, the gas sensors of the present disclosure exhibit unprecedented sensitivity, with a lower detection limit of about 5 ppb, as well as selectivity and stability.

Definitions

The terms recited below have been defined as described below. All other terms and phrases in this disclosure shall be construed according to their ordinary meaning as understood by one of skill in the art.

As used herein, "capturing" refers to the act of removing one or more chemical species from a bulk fluid composition (e.g., gas/vapor, liquid, and/or solid). For example, "capturing" may include, but is not limited to, interacting, bonding, diffusing, adsorbing, absorbing, reacting, and sieving, whether chemically, electronically, electrostatically, physically, or kinetically driven.

As used herein, "contacting" refers to the act of touching, making contact, or of bringing to immediate or close proximity, including at the atomic or molecular level, for example, to bring about a physiological reaction, a chemical reaction, or a physical change, e.g., in a solution, in a reaction mixture, in vitro, or in vivo. Accordingly, treating, tumbling, vibrating, shaking, mixing, and applying are forms of contacting to bring two or more components together.

As used herein, "deposit," "deposited," and/or "depositing" refers to growing, etching, doping, epitaxy, thermal oxidation, sputtering, casting, depositing, spin-coating, evaporating, applying, treating, and any other technique and/or method known to a person skilled in the art.

As used herein, "RE-fcu-MOF" refers to a metal-organic framework with fcu topology based on one or more rare earth metals.

Embodiments of the present disclosure describe a gas sensor comprising a gas-sensing material including a metal-organic framework with fcu topology and a substrate with a pair of electrodes proximate to the gas-sensing material, wherein the gas sensor is configured to detect gas. In some embodiments, a chemically stable MOF—namely, rare earth metal (RE) fcu-MOF—may be deposited directly on an interdigitated electrode substrate to measure a change in sensing film permittivity upon diffusion/adsorption of gases like $H_2S$ and $NH_3$ down to part per billions (ppb) and parts per millions (ppm) concentration levels, respectively. In many embodiments, impedance sensors may be selected due to their simple structure, compatibility with standard CMOS technology, and their ability to operate normally at room temperature assisting low-power applications. Impedance sensors (capacitive and/or resistive) sensors also may enable reliable and inexpensive miniaturization.

The gas sensor utilizes a metal-organic framework with fcu topology (fcu-MOF) as the gas-sensing material. In some embodiments, the fcu-MOF may passivate an active layer of a gas sensor. Alternatively, the gas-sensing material including an fcu-MOF may be selected to change in capacitance or resistance upon exposure to a toxic gas to be detected. The properties of the gas-sensing material may be adjusted by design of the material. Due to the presence of inorganic and organic molecules in the gas-sensing material, the pore size and chemical behavior of the gas-sensing material may be tuned to satisfy specific requirements, which make them more versatile than other porous inorganic materials. The gas-sensing material may serve as transducers by changing electronic, optical, and/or structural properties upon exposure to toxic gas. Examples of transduction mechanisms include change in dielectric constant, change in luminescence signal, structural swelling, and mass change. These types of changes may be detected via various methodologies, including by monitoring capacitance and/or resistance of the gas-sensing material. The versatility of the gas-sensing material due to the ability to tune pore size and chemical functionality, in additional to their exceptionally high surface area, may make these materials attractive for gas-sensing applications.

Metal-organic frameworks are crystalline porous materials composed of both organic and inorganic components arranged in a rigid periodic networked structure. Due to metal-organic framework's hybrid character and modular nature, metal-organic frameworks are regarded as porous materials with significant potential for addressing current challenges pertinent to energy and environmental sustainability. Metal-organic framework's unique tunability (e.g., porosity, nano-porosity, and surface area), which is not readily accessible in conventional porous materials (e.g., purely inorganic zeolites), offers great potential for their effective integration and exploration in various sensing applications. In addition, MOFs exhibit exceptional thermal and chemical stability and high adsorption selectivity and sensitivity towards $H_2S$ and $NH_3$.

The metal-organic frameworks with fcu topology of the present disclosure may be utilized as the gas-sensing material of the gas sensor for detecting toxic gas (e.g., $H_2S$ and $NH_3$). In many embodiments, the metal-organic frameworks with fcu topology are based on rare earth metals. The rare earth metals may include one or more of La, Ce, Pr, Nd, Sm, Eu, Gd, Dy, Ho, Er, Tm, Yb, Lu, Tb, and Y. RE-fcu-MOFs may be constructed from the assembly of rare earth hexanuclear molecular building blocks (MBBs) with a series of fluorinated and non-fluorinated, heterofunctional as well as fluorinated homofunctional linkers assisted by the modulator/structural directing agent (SDA) approach (e.g., 2-fluorobenzoic acid (2-FBA)). The connection of metal ions or clusters with multitopic organic linkers creates a regulated nano-space of MOFs for guest molecules through their molecular sieving effects, II-II interaction, hydrogen bonding, electrostatic interactions, etc. The nano-space in MOFs may recognize the size and shape of guest molecules.

The RE-fcu-MOF platform encloses two types of faces (e.g., tetrahedral and octahedral) that form a type of triangular window (delimited by linkers), constituting the sole entrance/access to the inner fcu-MOF pore system for guest molecules. Controlling the triangular window size and peripheral functionality may permit tuning of the pore size and adsorption properties of the resultant isoreticular fcu-MOF. In particular, reticular chemistry was utilized to tune the size and functionality of the triangular window of the RE-fcu-MOFs by substituting the parent longer ligand with relatively shorter and/or bulkier linkers (e.g., 1,4-naphthalene dicarboxylate or fumarate), permitting the assembly of isoretricular analogues of RE-fcu-MOFs with tuned adsorption/kinetic properties. Gas separation via a RE-fcu-MOF sorbent may be partially (synergy between both adsorption kinetics and adsorption thermodynamics) or totally driven by adsorption kinetics (molecular sieving).

The linker or ligand utilized in forming metal-organic frameworks may include small and/or bulky ligands. In many embodiments, the ligand may include fumaric acid and/or 1,4-naphthalene dicarboxylic acid.

A substrate may be proximate to the gas-sensing material. For example, in some embodiments, the gas-sensing material may be deposited as a thin film on the substrate. The substrate may include any type of semiconducting material (e.g., silicon, silicon wafers, etc.) and may include an electrode. In many embodiments, the substrate includes at least two electrodes arranged as interdigitated electrodes. Interdigitated electrodes provide a structural design that allows a variety of configurations that may improve chemical and/or biological sensing applications. For example, interdigitated electrodes may increase a surface area available for toxic gas molecules to diffuse, adsorb, and/or react. While many embodiments include interdigitated electrodes, any configuration of electrodes may be utilized.

The gas sensor is configured to detect toxic gas. In many embodiments, the gas sensor may detect toxic gas at room temperature. In many embodiments, the toxic gas is hydrogen sulfide ($H_2S$) and/or ammonia ($NH_3$). The gas sensor may include a detection sensitivity for $H_2S$ down to about 100 ppb, with a lower detection limit of about 5 ppb. In some embodiments, the gas-sensing material may be fabricated from an isoreticular RE-fcu-MOF—namely, fumarate (fum-fcu-MOF). The fum-fcu-MOF may exhibit a high detection selectivity towards $H_2S$ over $CH_4$, $NO_2$, $H_2$, and $C_7H_8$. In some embodiments, the gas-sensing material may be fabricated from an isoreticular RE-fcu-MOF—namely, naphthalene (naph-fcu-MOF). The naph-fcu-MOF may exhibit a high detection selectivity towards $NH_3$ over $CH_4$, $NO_2$, $H_2$, and $C_7H_8$ In an embodiment, the gas sensor detects $H_2S$ and/or $NH_3$ comprising: a gas-sensing material including a rare earth metal-organic framework with fcu topology (RE-fcu-MOF), wherein the ligand of the RE-fcu-MOF is one or more of fumaric acid and 1,4-napthalene dicarboxylic acid; and a substrate with a pair of electrodes, wherein the pair of electrodes is proximate to the gas-sensing material; wherein the gas sensor is configured to detect one or more of $H_2S$ and $NH_3$.

FIG. 1 is a schematic diagram of an optimized solvothermal preparation approach of a fumarate-based fcu-MOF (fum-fcu-MOF) thin film on an interdigitated electrode (IDE), according to one or more embodiments of the present disclosure. As shown in FIG. 1, hexanuclear clusters may be bridged by organic linkers, such as fumarate, sufficient to form a fumarate-based fcu-MOF deposited as a thin film on an interdigitated electrode. The triangular windows provide the only access point for guest molecules, such as toxic gas.

Figure 2:
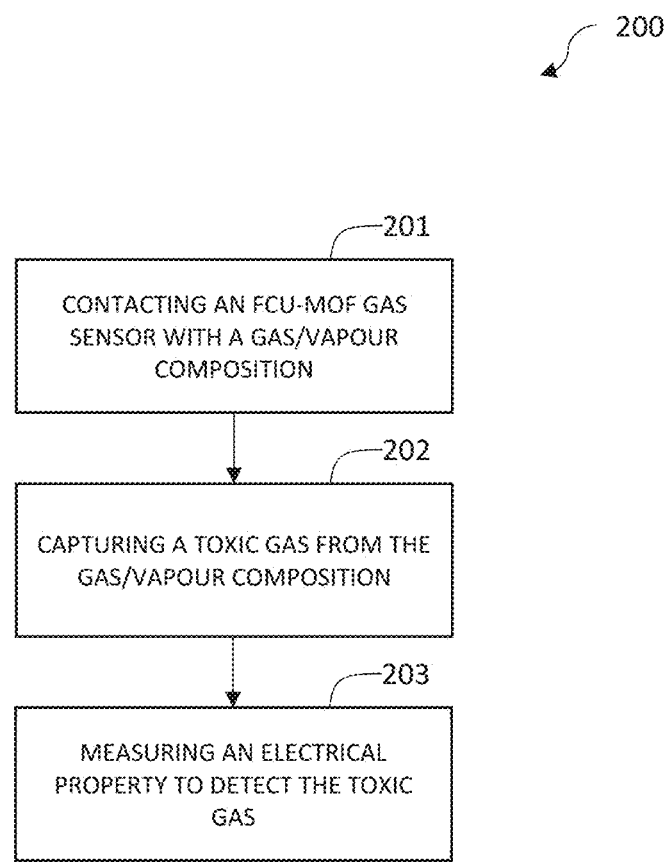
FIG. 2 is a flowchart of a method of detecting gas, according to one or more embodiments of the present disclosure.

FIG. 2 is a flowchart of a method of detecting gas, according to one or more embodiments of the present disclosure. Any of the embodiments discussed above may be utilized here.

At step 201, a gas sensor including a metal-organic framework with fcu topology is contacted with a gas/vapour composition. The gas/vapour composition may include toxic components and non-toxic components. The toxic components and non-toxic components may be present in the gas/vapour composition in a gas/vapor phase. In many embodiments, the toxic component of the gas/vapour composition may include $H_2S$ and/or $NH_3$ as a toxic gas/vapor. The non-toxic component of the gas/vapour composition may include one or more of $H_2S$, $CH_4$, $NO_2$, $H_2$, and $C_7H_8$. In some embodiments, the gas/vapour composition may include only one or more toxic components. In other embodiments, the gas/vapour composition may include only non-toxic components. In other embodiments, the gas/vapour composition includes any combination of toxic and non-toxic components in any phase (e.g., solid, gas/vapour, liquid).

At step 202, one or more toxic gases are captured from the gas/vapour composition. In many embodiments, the toxic gas may be captured in the gas-sensing sensing material including the metal-organic framework with fcu topology. Toxic gas may be captured via diffusion, adsorption, and/or chemical reaction. In other embodiments, toxic gas may be captured via diffusion, adsorption, and/or chemical reaction of the toxic gas in a sensing region. The sensing region may include one or more of the gas sensor, gas-sensing material, metal-organic framework, electrode(s), and substrate. The gas-sensing material including the metal-organic framework with fcu topology may be tuned to a particular application or desired performance characteristics. For example, the metal-organic framework may be tuned via selection of the metal, ligand and/or linker, and topology to increase a selectivity and/or sensitivity of the gas sensor towards capturing one or more toxic gases.

At step 203, an electrical property is measured to detect toxic gas. In many embodiments, upon being exposed to toxic gas, the gas sensor produces an electrical variation and/or measurable electrical property that may be utilized to detect a presence of toxic gas. In some embodiments, the electrical property being monitored and/or measured may include the impedance (real and imaginary components), resistance, and/or capacitance of the gas-sensing material. For example, a change in capacitance may be due to a change in dielectric constant and/or swelling of the gas-sensing material upon exposure to toxic gas. In other embodiments, toxic gas may react on an electrode via oxidation and/or reduction to produce a measureable electrical property (e.g., an electrical current) that may be utilized to detect a presence of toxic gas and/or measure a concentration of toxic gas, among other things.

In an embodiment, the method of detecting gas comprises contacting a gas sensor including a rare earth metal-organic framework with fcu topology (RE-fcu-MOF) with a fluid composition including one or more of $H_2S$ and $NH_3$ and at least one other chemical species; capturing one or more of $H_2S$ and $NH_3$ from the fluid composition; and measuring an electrical property to detect a presence of one or more of $H_2S$ and $NH_3$.

The following Examples are intended to illustrate the above invention and should not be construed as to narrow its scope. One skilled in the art will readily recognize that the Examiners suggest many other ways in which the invention could be practiced. It should be understand that numerous variations and modifications may be made while remaining within the scope of the invention.

EXAMPLE 1

$H_2S$ Sensors: Fumarate-Based fcu-MOF Thin Film Grown on a Capacitive Interdigitated Electrode Gas/vapor sensing is becoming an important emerging research field and is of high interest to industry. The greatest demand for effective gas/vapor sensors may include oil/gas platforms and refineries, manufacturing processes, and firefighting. For example, gas/vapor sensors may be used for detecting toxic, combustible, and flammable gases; air, environment and/or food quality control; and non-invasive biomedical applications.

An example of a particularly relevant toxic gas is hydrogen sulfide. Hydrogen sulfide is considered a dangerous toxic gas with a characteristically unpleasant odor. Various industrial activities may produce large quantities of hydrogen sulfide, including, for example, petroleum and natural gas drilling/refining, as well as waste water treatment. For example, it is naturally abundant in crude petroleum, natural gas, landfill gas, and hot springs. In addition, it is often released during the decay of organic matter and/or bacterial breakdown of sewage.

As confirmed by various occupational safety and health institutions, exposure to hydrogen sulfide in concentrations above about 2-5 ppm may lead to negative health effects, especially with respect to the human respiratory system. Exposure above about 100 ppm may lead to neurological sequelae, and exposure above about 1000-2000 ppm may even lead to instantaneous death. According to the Scientific Advisory Board on Toxic Air Pollutants, regulations for acceptable ambient levels of hydrogen sulfide should be in the range of about 100 ppb. Hydrogen sulfide may also cause a malodor-nuisance problem at relatively low concentrations.

Despite the abundance of hydrogen sulfide and its negative health effects, the continuous monitoring of low hydrogen sulfide concentrations remains a challenge in industry. Hydrogen sulfide monitoring in environmental samples is most frequently undertaken using gas chromatography-based methods. Although these techniques may be precise, application thereof requires a multi-stage testing protocol, making it inconvenient to monitor short-term variations in hydrogen sulfide levels arising from changes in environmental conditions.

Chemical sensors have been used in various application fields (e.g., safety, the chemical industry, emissions monitoring, the automotive industry, and home-safety alarms). Different types of chemical sensors have been developed and employed for the real-time monitoring of toxic hydrogen sulfide. These sensors have been primarily based on using semiconducting metal oxide, electrochemical sensors with both liquid and solid electrolyte, optical sensors, and sensor arrays. These sensors' sensing principles can vary significantly, depending on the material type and fabrication. The development of most hydrogen sulfide sensors is based on principles of colorimetry and spectroscopy (i.e., absorption and fluorescence). However, colorimetric sensors cannot be easily integrated with electronics in a miniaturized microsystem. Interdigitated electrodes may be utilized to harness these features, in addition to their structural design (which allows for a variety of configurations that potentially improve chemical or biological sensing applications). Furthermore, the use of a standard lithography procedure in the fabrication process makes it possible to miniaturize and lower the cost of IDE sensors, which in turn enables working with a low volume of sample, and they can be easily integrated with electronics. The IDEs offer the prospect to access the requisite low-power sensing platform, such as lab-on-chip applications. Moreover, sensor performance depends largely on the coated or deposited sensing layer. For example, a detection limit of ppm of $H_2S$ was measured at room temperature using Cu nanoparticles decorated SWCNTs or Cu—ZnO nanowires. Detection limits of 500 and 100 ppb were recently achieved using a $Cu_2O/SnO_2$ film and graphene flakes/$WO_3$ nanofibers, respectively.

Figure 3A:
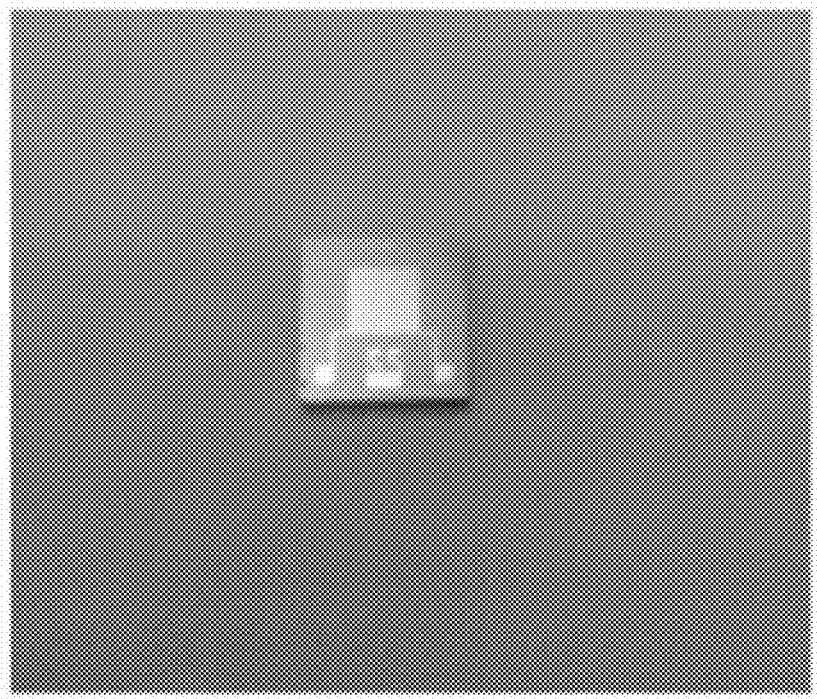
FIGS. 3a-3b are optical microscopy images of a fabricated interdigitated electrode device (3a) and an electrode area (enlarged) (3b), according to one or more embodiments of the present disclosure.
Figure 3B:

An isoreticular fumarate-based RE-fcu-MOF (FIG. 1) was fabricated as a thin film sensing layer on capacitive interdigitated electrodes (IDEs) (FIGS. 3a-3b).

The IDE sensors were fabricated using clean room technologies. In particular, IDEs were fabricated on silicon wafer. A 2 μm oxide layer was thermally grown for electrical isolation. A layer of 10 nm Ti and 300 nm Au was first deposited via physical vapor deposition (PVD) in an ESC reactive and metal sputter system. Photolithography was then used to pattern the electrodes. The metal layer was patterned by dry etching using Oxford Insruments Plasma-Lab System and the exposed oxide thickness was further verified using Nanospec 6100 Reflectometer to ensure that the metal layer was properly etched. The IDEs were designed with 4 μm fingers and 5 μm spaces. Two Au wires and contact pads were patterned to perform the electrical measurements.

Thin films of the fum-fcu-MOFs were prepared solvothermally by heating solution containing fumaric acid (10.1 mg, 0.087 mmol), $Y(NO_3)_3 \cdot 6H_2O$ (33.4 mg, 0.087 mmol), 2-fluorobenzoic acid (195.0 mg, 1.392 mmol) DMF (2.7 mL), and deionized $H_2O$ (0.5 mL), were combined in a 20 mL scintillation vial. Prior to the growth of the MOF thin film, the IDEs were functionalized with an OH-terminated self-assembled monolayer (SAM) (11-mercaptoundecanol). That is, a pre-functionalized IDE chip with the MUD SAM was placed inside the vial and sealed and heated to about 105° C. for about 36 hours and then cooled to about room temperature. The IDE chip was collected and washed with about 10 mL of anhydrous DMF and immersed in 10 mL of ethanol for about 3 days, during which time the ethanol was replaced three times per day.

Figure 4:
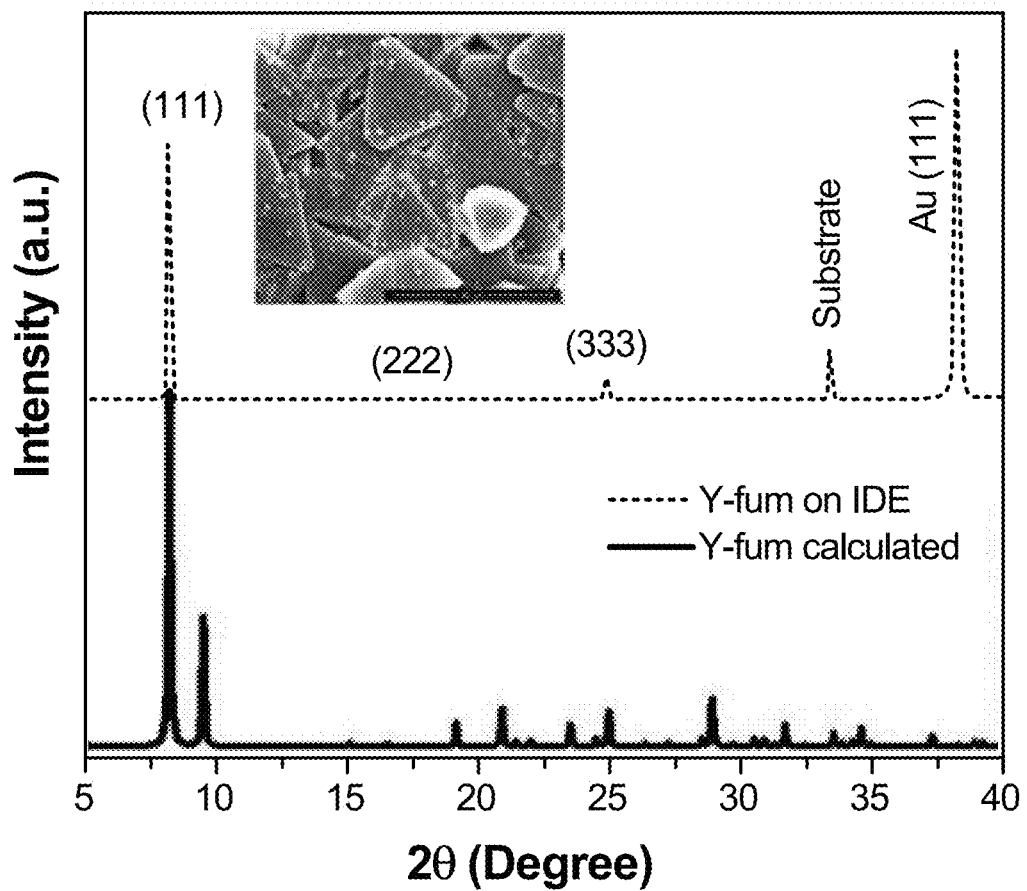
FIG. 4 is a graphical view of calculated X-ray diffraction (XRD) patterns of fum-fcu-MOF (black) and its thin film grown on the interdigitated electrode substrate (red), with a scanning electron microscopy (SEM) image of the fum-fcu-MOF thin film in the inset, according to one or more embodiments of the present disclosure.
Figure 5:
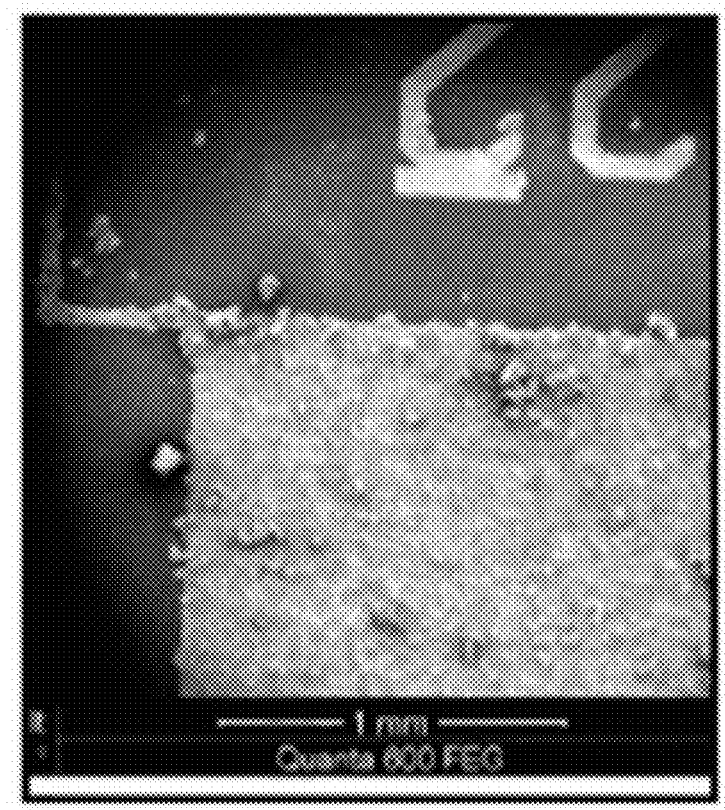
FIG. 5 is a scanning electron microscopy image of a fabricated fum-fcu-MOF thin film on an interdigitated electrode device, according to one or more embodiments of the present disclosure.

Using the in situ crystallization method under the predetermined reaction conditions for the construction of the RE-fcu-MOF and in the presence of fumaric acid, a homogenous fumarate-based fcu-MOF (fum-fcu-MOF) thin film was successfully grown for the first time. (FIG. 1). The resultant thin-film crystallinity and preferential orientation along the [111] direction were confirmed by out-of-plane X-ray diffraction (XRD) measurements, as shown in FIG. 4. In addition, the scanning electron microscopy (SEM) images (FIG. 5) corroborate the formation of a close thin film of these highly oriented small crystals (see inset in FIG. 4). Markedly this approach to the growth of fum-fcu-MOF thin films in preferential growth orientation afforded the looked-for exposure of the triangular windows of the fcu-MOF structure (FIG. 1), affording sole access to the network pore system. Correspondingly, the successful growth of the fum-fcu-MOF crystals directly on the IDE substrate allowed it to be used for monitoring and measuring the change in sensing film permittivity upon gas/vapor adsorption.

Figure 6:
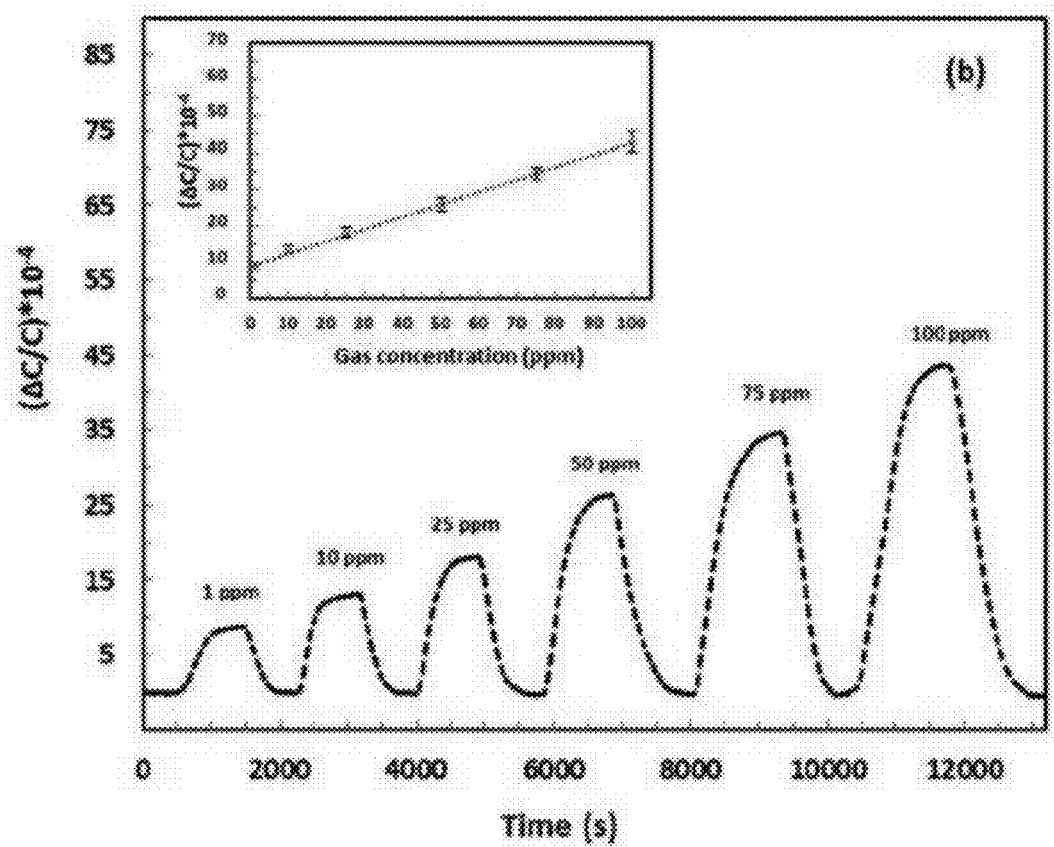
FIG. 6 is a graphical view of a change in capacitance as a function of time showing detection of $H_2S$ at concentrations ranging from about 100 ppb to about 1000 ppb with the corresponding linear range in the inset, according to one or more embodiments of the present disclosure.
Figure 7:
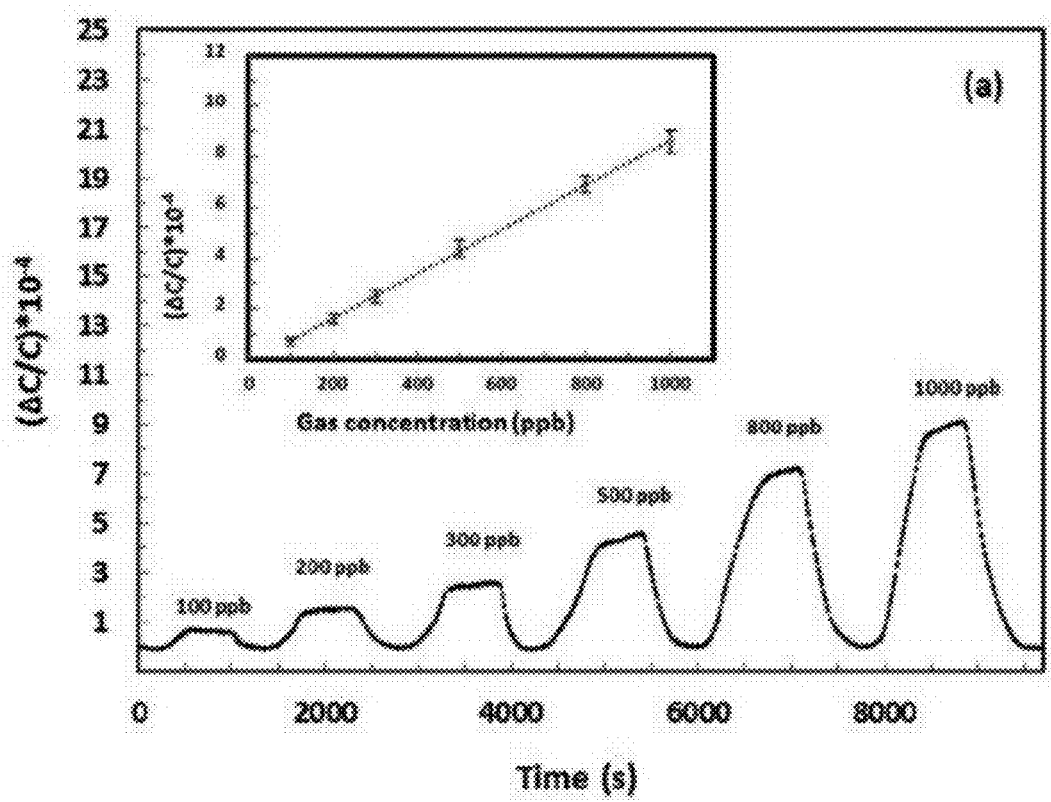
FIG. 7 is a graphical view of a change in capacitance as a function of time showing detection of $H_2S$ at concentrations ranging from about 1 ppm to about 100 ppm with the corresponding linear range in the inset, according to one or more embodiments of the present disclosure.

Capacitive sensors were selected because of their simple structure, compatibility with standard complementary metal-oxide-semiconductor technology, and ability to readily operate at room temperature (a feature highly beneficial for reducing both power and costs). In addition, capacitive sensors enable miniaturization reliably and inexpensively. The sensing properties of fum-fcu-MOF thin film on capacitive IDEs were investigated for different types of gases/vapours, including $CH_4$, $NO_2$, $H_2$, toluene ($C_7H_8$), and $H_2S$. The gas-sensing tests were performed using the Lab-VIEW fully automated measurement system. The coated sensor was placed inside the detection chamber and connected to the CLR meter to detect the capacitive change. The samples were first activated under vacuum for one hour; the chamber was later purged with pure nitrogen. Nitrogen gas was used as a carrier gas to dilute the $H_2S$ to the desired concentration. Two concentration ranges were utilized: a ppm range from about 1 to about 100 ppm and a ppb level range from about 100 to about 1000 ppb. The fum-fcu-MOF-coated sensor performed well in both ppm and ppb ranges, as shown in FIGS. 6-7. The fum-fcu-MOF sensors detected $H_2S$ at the ppm range from about 1 to about 100 ppm, with a linear response (FIG. 6 and inset). Most importantly, fum-fcu-MOF performed very well at a ppb level down to about 100 ppb, with a linear response (inset of FIG. 7) and a detection limit of about 5.4 ppb. The detection limits in both ppm and ppb levels were calculated based on the root-mean-square deviation method.

Figure 8:
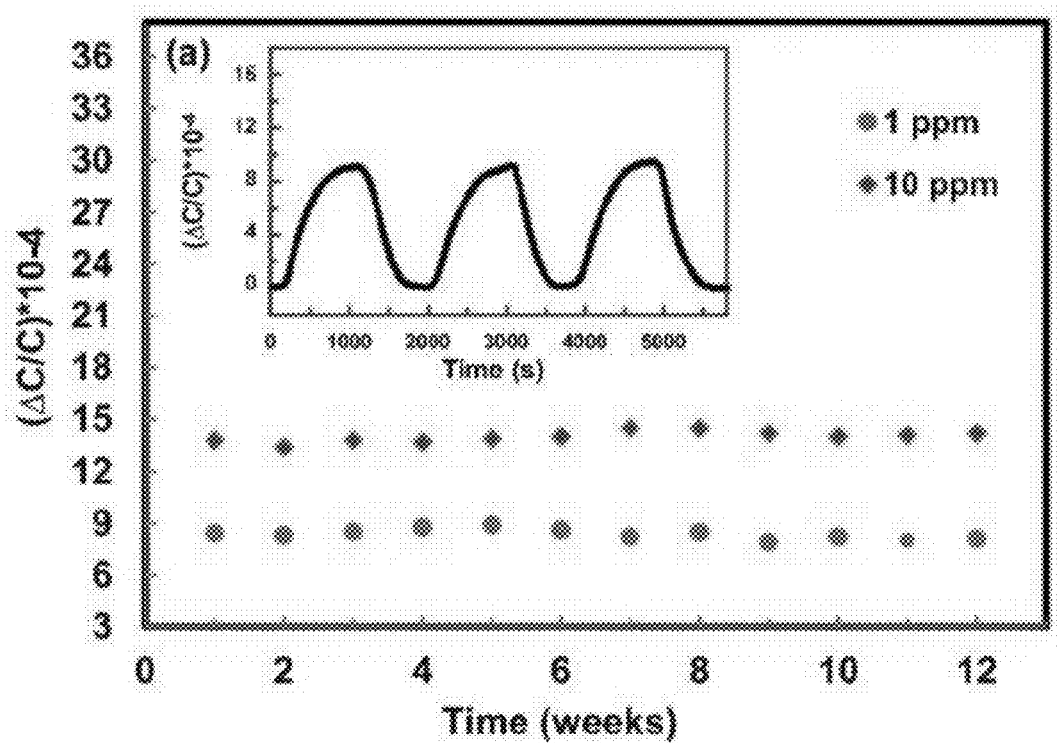
FIG. 8 is a graphical view of a change in capacitance as a function of time showing stability performance of fum-fcu-MOF over 12 weeks with reproducibility cycles for detection of 1 ppm of $H_2S$ in the inset, according to one or more embodiments of the present disclosure.
Figure 9:
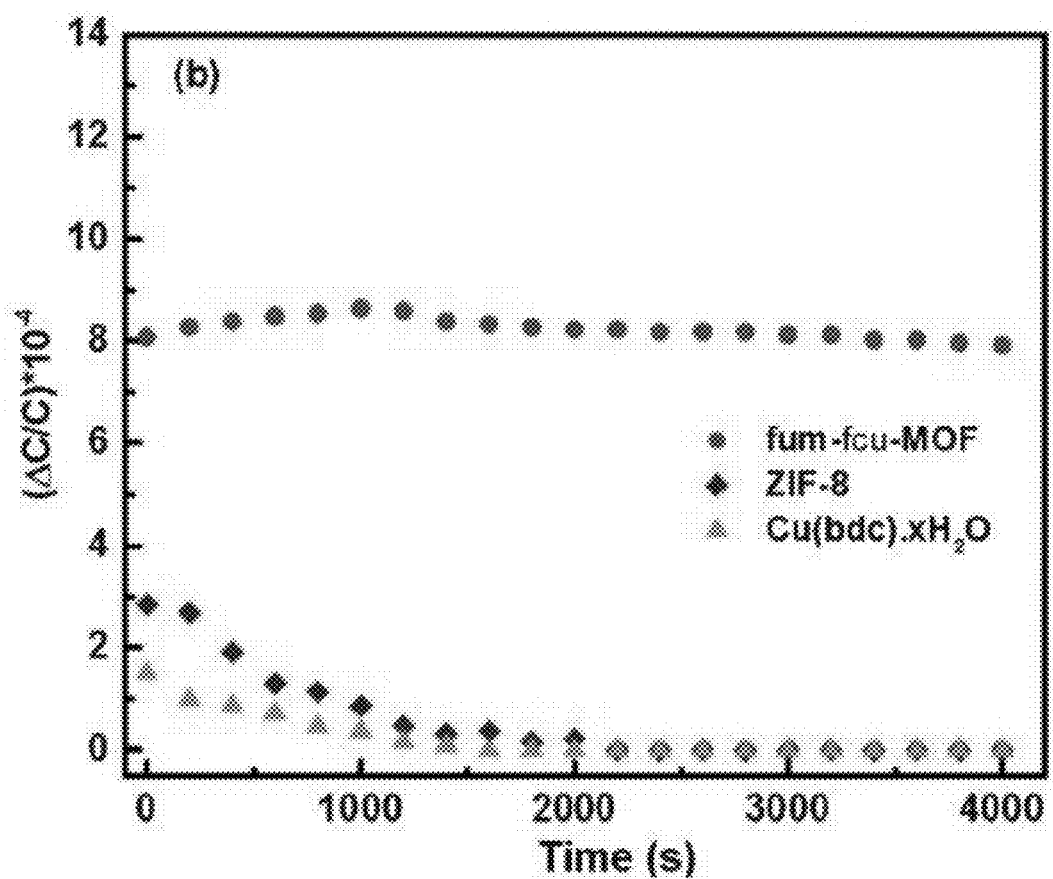
FIG. 9 is a graphical view of a change in capacitance as a function of time showing stability performance of fum-fcu-MOF, ZIF-8, and 2D $Cu(bdc).xH_2O$ MOF, according to one or more embodiments of the present disclosure.
Figure 10:
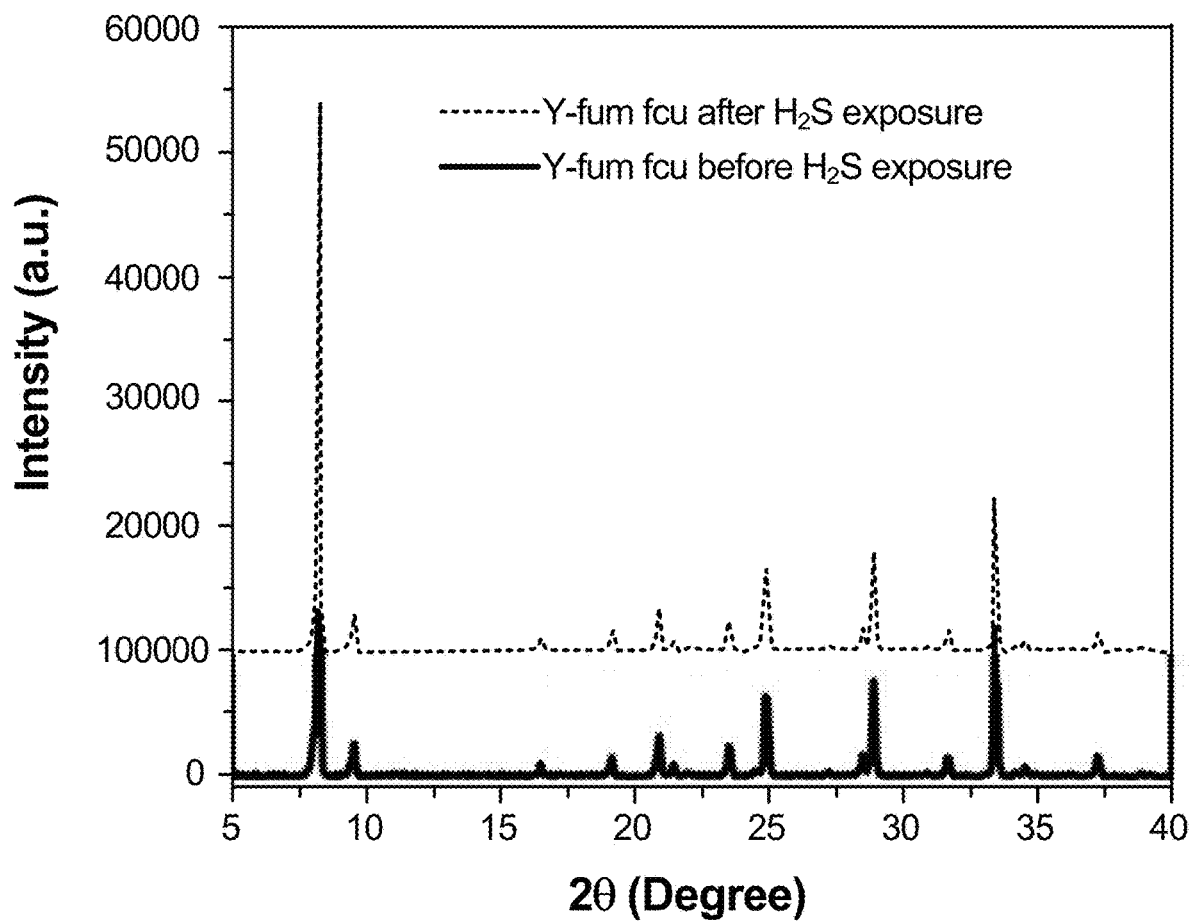
FIG. 10 is a graphical view of a powder X-ray diffraction image of fum-fcu-MOF before and after exposure to $H_2S$, according to one or more embodiments of the present disclosure.
Figure 11:
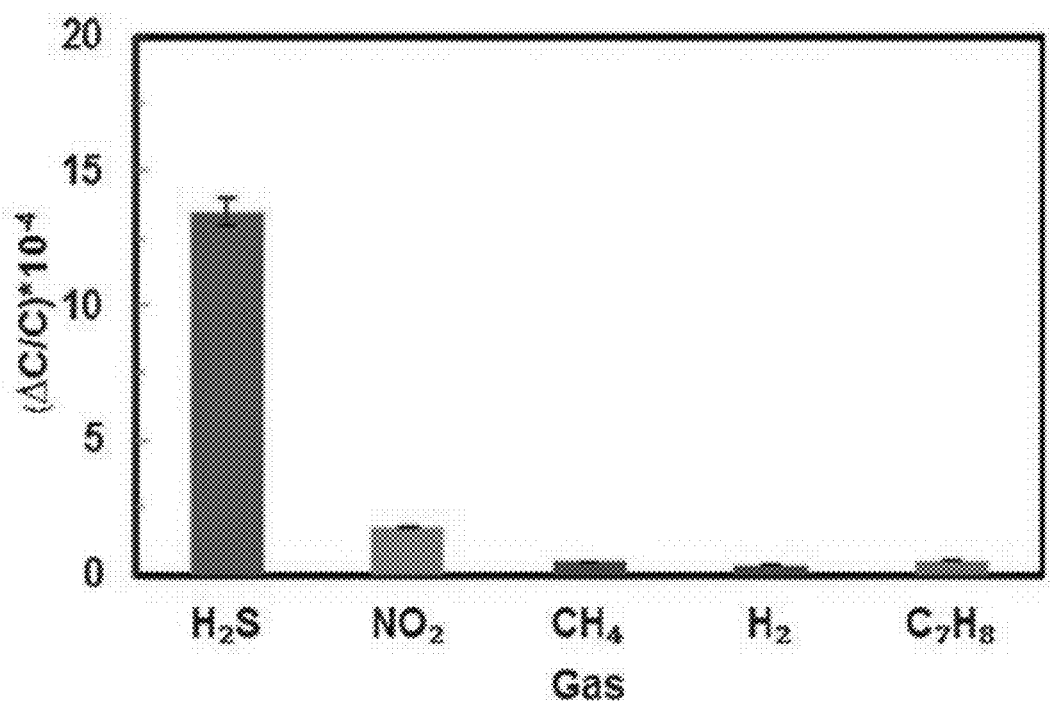
FIG. 11 is a graphical view of a change in capacitance for a variety of gases, showing a selectivity of the fum-fcu-MOF sensor to $H_2S$ in the presence of $NO_2$, $CH_4$, $H_2$, and $C_7H_8$ at 10 ppm, according to one or more embodiments of the present disclosure.

The stability of the fum-fcu-MOF sensor for $H_2S$ detection at room temperature was demonstrated using two methods. The first method involved reproducibility tests, through which the performance of the sensors for detecting about 1 ppm and about 10 ppm of $H_2S$ within a testing period of three months (FIG. 8) was observed. The second method entailed performing reproducibility cycles (inset of FIG. 8), where it was clearly evidenced that the detections levels were steady/stable and uniform over the range of various cycles. As shown in FIG. 9, the sensors coated, each with a different type of MOF (fum-fcu-MOF, ZIF-8, and Cu(bdc).$xH_2O$), were exposed to about 1 ppm of $H_2S$. As shown in FIG. 9, while fum-fcu-MOF showed a very good stability (with slight variation), the performance of the other MOFs (namely, 2D Cu(bdc).$xH_2O$ and ZIF-8) were clearly not stable, with Cu(bdc).$xH_2O$ being the least stable. The low stability of these MOFs was plausibly due to the degradation of the materials as a result of the metal sulfide formation upon prolonged exposure to $H_2S$. In turn, the distinctive stability of fum-fcu-MOF was the result of RE hexanuclear cluster bridged by shorter and rigid linkers and thus prohibiting the metal sulfide formation. Particularly, the detection signal for the fum-fcu-MOF is relatively much higher (e.g., about three to four times) than the other two types of MOFs tested, which agreed well with the $H_2S$ stability tests done in the associated bulk MOF materials (FIG. 10). These tests demonstrated the stability of the fum-fcu-MOF sensor and its superior $H_2S$ detection relative to other MOFs. The selectivity of the fum-fcu-MOF sensor to $H_2S$ was studied and evaluated in the presence of other gases and volatile organics, fcu-MOF showed an excellent selectivity for $H_2S$ over the other gases/vapors tested. While a slight cross sensitivity was detected with compounds such as nitrogen dioxide ($NO_2$), methane ($CH_4$), hydrogen ($H_2$), and toluene ($C_7H_8$). As shown in FIG. 11, the most significant other signal was observed in relation to $NO_2$, whereas almost negligible signals were observed for $CH_4$, $H_2$, and $C_7H_8$; furthermore, the $H_2S$ signal was almost six times that of the corresponding signal for $NO_2$. These results confirm the enhanced selectivity of $H_2S$ in the presence of other gases/vapors with different physical and/or chemical properties.

In conclusion, the performance of the fum-fcu-MOF as a sensing layer, a thin film on a capacitive IDE sensor, for $H_2S$ detection at room temperature was demonstrated. Principally, the fum-fcu-MOF offers a distinctive $H_2S$ detection to concentrations down to about 100 ppb with a limit of detection of about 5.4 ppb. Furthermore, the good linearity vis-à-vis both ppb and ppm ranges offers great prospective for the fabrication not a sensor with additional functionalities and applications (e.g., for switch sensors). The stability of the fum-fcu-MOF sensor was supported and revealed using different methods, which attest to its greater chemical stability as compared to other types of MOF, such as ZIF-8 and Cu(bdc).$xH_2O$. The signal intensity associated with the fum-fcu-MOF's $H_2S$ detection was compared to the corresponding signal intensity for relevant gases/vapors, such as nitrogen oxide, methane, hydrogen, and toluene and revealed a distinctive and selective sensitivity of the fum-fcu-MOF towards $H_2S$. This sensing property of the fum-fcu-MOF allows deployment of MOFs as practical sensors for a variety of applications.

EXAMPLE 2

Detection of $NH_3$ Via Impedance Sensors Thin-Film Coated with MOFs

Ammonia is a natural gas present throughout the atmosphere. The relatively low concentrations—ranging from about low-ppb to sub-ppb levels—have been significantly higher in the past. Today, most of the ammonia in our atmosphere is emitted directly or indirectly by human activity. A major source of ammonia is combustion, both from chemical plants and motor vehicles Ammonia is produced by the chemical industry for the production of fertilizers and for the use in refrigeration systems. The total emission of ammonia from combustion is about 2.1-8.1 Tg/year. High concentrations of ammonia form a threat to the human health. The lower limit of human ammonia perception by smell is tabulated to be around 50 ppm, corresponding to about 40 μg/m³. However, even below this limit, ammonia is irritating to the respiratory system, skin and eyes. The long-term allowed concentration that people may work in is set to be about 20 ppm Immediate and severe irritation of the nose and throat occurs at 500 ppm. Exposure to high ammonia concentrations, 1000 ppm or more, can cause pulmonary edema; accumulation of fluid in the lungs. Extremely high concentrations, 5000-10,000 ppm, are suggested lethal within 5-10 min.

There are many ways to detect ammonia. High concentrations are easy to detect because the gas has a very penetrating odor. With respect to other odorous gasses, the human nose is very sensitive to ammonia. To quantify the ammonia concentration or determine lower concentrations of ammonia, the human nose fails. However, in many occasions, the ammonia concentration has to be known, even at ultra-low concentrations of less than parts per billion in air (ppb). There are four major areas that are of interest for measuring ammonia concentrations; environmental, automotive, chemical industry and medical diagnostics. The concentration levels of interest depend on the different application areas. There are many principles for measuring ammonia and different sensors are used in the exhaust pipe of automobiles than for measuring ultra-low concentrations of ambient ammonia for environmental monitoring. The most frequently used techniques in commercial ammonia detectors are metal-oxide gas sensors, catalytic ammonia detectors, conducting polymer ammonia analyzers and optical ammonia detection techniques. There are other indirect systems using gas samplers and specific chemical reactions to make a selective ammonia analyzer.

Metal-organic frameworks exhibit high potential for applications such as gas storage/purification, catalysis, and sensing based on their tunable nano-porosity and high surface area. The connection of metal ions or clusters with multitopic organic linkers creates a regulated nano-space within the extended crystalline structures. The guest molecules can be incorporated into the nano-space of MOFs through their molecular sieving effects, π-π interaction, hydrogen bonding, and electrostatic interactions, etc. The nano-space in MOFs can recognize the size and shape of guest molecules, and their high surface-areas make them promising candidates for a variety of sensing applications. MOFs may be integrated into devices such as quartz crystal microbalance (QCM), surface plasmon resonance (SPR) spectroscopy, surface acoustic wave devices, and microcantilevers for chemical detection of small guest molecules.

Figure 12:
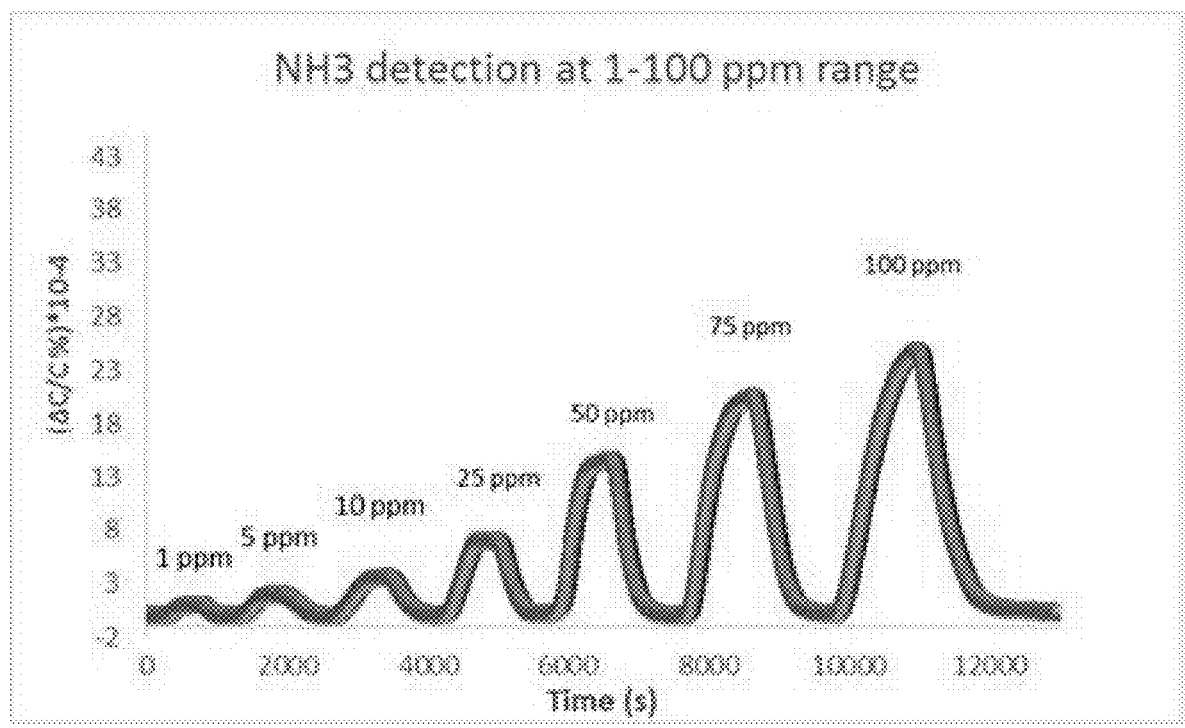
FIG. 12 is a graphical view of a change in capacitance as a function of time showing detection of $NH_3$ for a naph-fcu-MOF sensor at concentrations ranging from about 1 ppm to about 100 ppm, according to one or more embodiments of the present disclosure.
Figure 13:
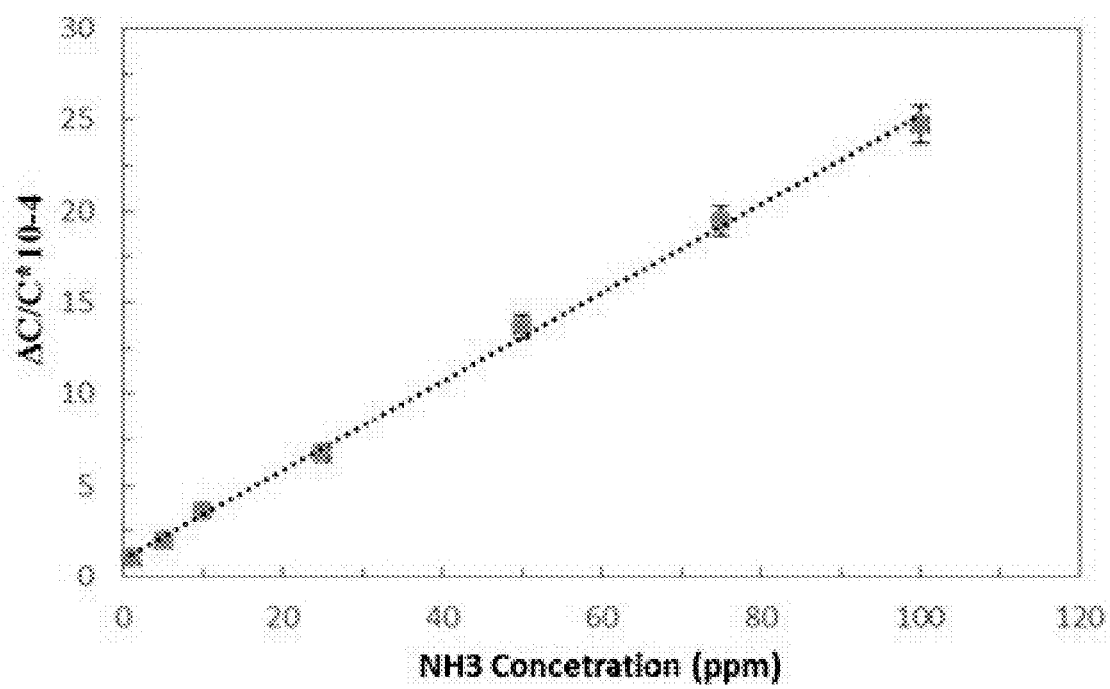
FIG. 13 is a graphical view of a change in capacitance for a naph-fcu-MOF sensor as a function of $NH_3$ concentration (ppm) showing a linear dependence, according to one or more embodiments of the present disclosure.
Figure 14:
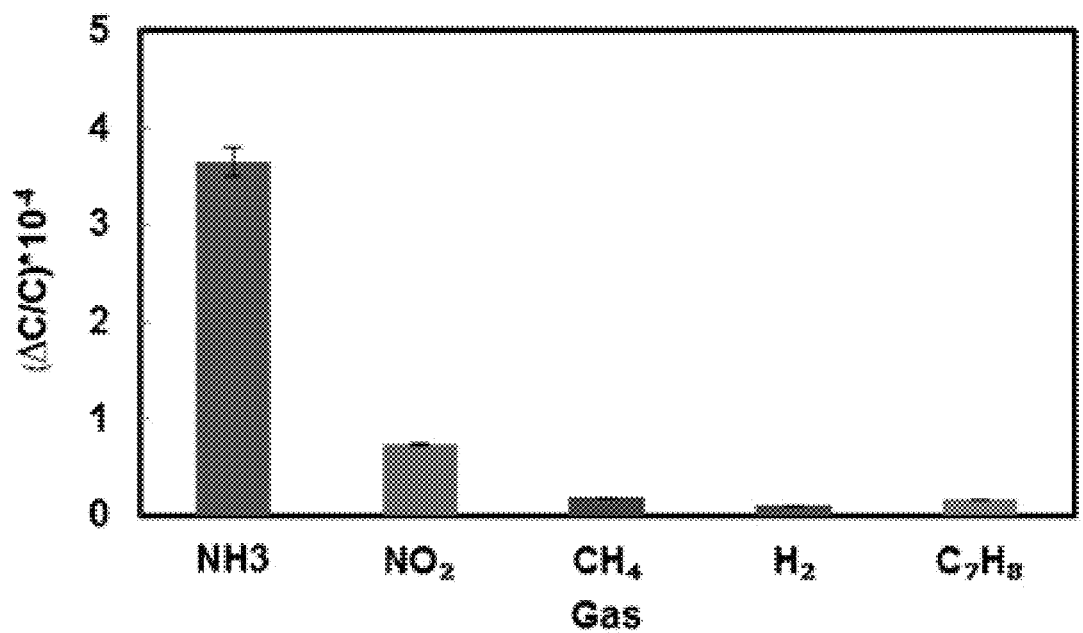
FIG. 14 is a graphical view of a change in capacitance for a variety of gases, showing a selectivity of the naph-fcu-MOF for sensor towards $NH_3$ in the presence of $NO_2$, $CH_4$, $H_2$, and $C_7H_8$ at 10 ppm, according to one or more embodiments of the present disclosure.
Figure 15:
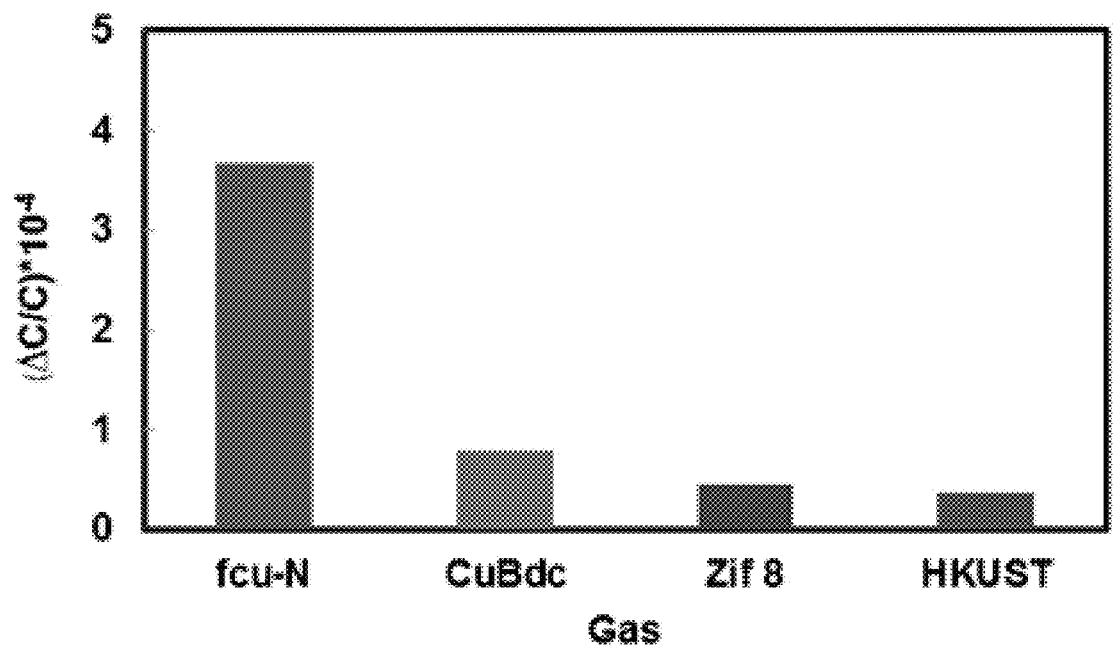
FIG. 15 is graphical view of a change in capacitance for a variety of MOFs, showing stability performance of naph-fcu-MOF compared to ZIF-8 and 2D $Cu(bdc).xH_2O$ MOF, according to one or more embodiments of the present disclosure.

A chemically stable MOF—namely RE-fcu-MOF—based the 1,4-naphtalene dicarboxylic acid (naph-fcu-MOF) was deposited directly on an interdigitated electrodes (IDE) substrate to measure a change in sensing film permittivity upon diffusion/adsorption of $NH_3$ down to about one part per million (ppm) concentration levels (FIGS. 12-13). The gas-sensing material including RE-fcu-MOF has also shown high selectivity for $NH_3$ over other gases and other types of MOFs (FIGS. 14-15). Impedance sensors were selected because of their simple structure, compatibility with standard CMOS technology and their ability to operate normally at room temperature assisting low-power applications. In addition, impedance (capacitive and/or resistive) sensors enable miniaturization reliably and inexpensively.

Other embodiments of the present disclosure are possible. Although the description above contains much specificity, these should not be construed as limiting the scope of the disclosure, but as merely providing illustrations of some of the presently preferred embodiments of this disclosure. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form various embodiments. Thus, it is intended that the scope of at least some of the present disclosure should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

The foregoing description of various preferred embodiments of the disclosure have been presented for purposes of illustration and description. It is not intended to be exhaustive or to limit the disclosure to the precise embodiments, and obviously many modifications and variations are possible in light of the above teaching. The example embodiments, as described above, were chosen and described in order to best explain the principles of the disclosure and its practical application to thereby enable others skilled in the art to best utilize the disclosure in various embodiments and with various modifications as are suited to the particular use contemplated. It is intended that the scope of the disclosure be defined by the claims appended hereto Various examples have been described. These and other examples are within the scope of the following claims.

What is claimed is:

1. A gas sensor for detecting $H_2S$ and/or $NH_3$, comprising:
a gas-sensing material including a rare earth metal-organic framework with fcu topology (RE-fcu-MOF), wherein the RE-fcu-MOF includes a bridging ligand and wherein the bridging ligand is one or more of fumarate and 1,4-naphthalene dicarboxylate; and
a substrate with a pair of electrodes, wherein the pair of electrodes is proximate to the gas-sensing material;
wherein the gas sensor is configured to detect one or more of $H_2S$ and $NH_3$.

2. The gas sensor of claim 1, wherein the gas sensor is an impedance sensor.

3. The gas sensor of claim 1, wherein the gas sensor is a capacitive sensor and/or a resistive sensor.

4. The gas sensor of claim 1, wherein the gas sensor detects one or more of $H_2S$ and $NH_3$ via one or more of diffusion, adsorption, and chemical reaction of $H_2S$ and/or $NH_3$ in the gas-sensing material.

5. The gas sensor of claim 1, wherein the gas sensor exhibits a selectivity towards $H_2S$ and/or $NH_3$ over one or more of $NO_2$, $CH_4$, $H_2$, and $C_7H_8$.

6. The gas sensor of claim 1, wherein the gas sensor detects one or more of $H_2S$ and $NH_3$ at concentrations down to about 100 ppb.

7. The gas sensor of claim 1, wherein the gas sensor exhibits a limit of $H_2S$ and/or $NH_3$ detection of about 5 ppb.

8. The gas sensor of claim 1, wherein the gas-sensing material is fabricated as a thin-film on the substrate.

9. The gas sensor of claim 1, wherein the RE-fcu-MOF is based on hexanuclear rare earth-metal clusters bridged by the bridging ligands.

10. The gas sensor of claim 1, wherein the bridging ligands that bridge the hexanuclear rare earth-metal clusters prevent metal sulfide formation and enhance the stability of the gas sensor.

11. The gas sensor of claim 1, wherein the rare earth metals include one or more of La, Ce, Pr, Nd, Sm, Eu, Gd, Dy, Ho, Er, Tm, Yb, Lu, Tb, and Y.

12. The gas sensor of claim 1, wherein the substrate is an interdigitated electrode substrate.

13. The gas sensor of claim 1, wherein the gas sensor operates at about room temperature.

14. A method of detecting gas, comprising:
contacting a gas-sensing material including a rare earth metal-organic framework with fcu topology (RE-fcu-MOF) with a fluid composition including one or more of $H_2S$ and $NH_3$ and at least one other chemical species, wherein the RE-fcu-MOF includes a bridging ligand and a substrate with a pair of electrodes, wherein the bridging ligand is one or more of fumarate and 1,4-naphthalene dicarboxylate, wherein the pair of electrodes is proximate to the gas-sensing material, and wherein the gas sensing material is configured to detect one or more of $H_2S$ and $NH3$;
capturing one or more of $H_2S$ and $NH_3$ from the fluid composition; and
measuring an electrical property to detect a presence of one or more of $H_2S$ and $NH_3$.

15. The method of claim 14, wherein the rare earth metals of the RE-fcu-MOF include one or more of La, Ce, Pr, Nd, Sm, Eu, Gd, Dy, Ho, Er, Tm, Yb, Lu, Tb, and Y.

16. The method of claim 14, wherein one or more of $H_2S$ and $NH_3$ is captured via one or more of diffusion, adsorption, and chemical reaction with the RE-fcu-MOF.

17. The method of claim 14, wherein the measured electrical property includes one or more of a change in capacitance, resistance, and permittivity.

18. The method of claim 14, wherein the other chemical species include one or more of $CH_4$, $NO_2$, $H_2$, and toluene.

\* \* \* \* \*